United States Patent [19]

Moore

[11] Patent Number: Plant 7,055

[45] Date of Patent: Nov. 14, 1989

[54] MINIATURE ROSE PLANT 'MORJOYC'

[75] Inventor: Ralph S. Moore, Visalia, Calif.

[73] Assignee: Sequoia Nursery, Calif.

[21] Appl. No.: 252,904

[22] Filed: Oct. 3, 1988

[51] Int. Cl.[4] ..... A01H 5/00

[52] U.S. Cl. ..... Plt./7

[58] Field of Search ..... Plt. 7

*Primary Examiner*—James R. Feyrer

[57] ABSTRACT

The subject of the present disclosure is a new and distinct variety of miniature rose plant characterized by bright orange buds and flowers of good substance and keeping qualities.

1 Drawing Sheet

The present invention relates to a new and distinct variety of hardy, dwarf, bush type rose plant of the miniature class: the variety being primarily characterized—as to novelty—by bright orange buds and flowers. The general color effect being bright orange to apricot.

The variety is further characterized by:

An abundance of bloom, with flowers, on mature plant, borne both singly and several together in loose spray or cluster.

Light fragrance.

A plant which is vigorous, of rounded, somewhat upright shape with semi-glossy to matt, small foliage with pointed leaflets; the buds and flowers being similar in form to Sheri Anne (Miniature—U.S. Plant Pat. No. 3,826).

The plant, which has a normal height of 14 inches or more, can easily be maintained at lesser height by occasional trimming.

A plant which grows and blooms satisfactorily both in greenhouse and outdoors; is good for growing in pots; and provides excellent garden decoration as well as cut flowers.

The present variety of miniature rose was originated by me at Sequoia Nursery, located at Visalia, Calif., under conditions of careful control and observation, as a cross between a climbing (un-named seedling) yellow miniature (Little Darling/Florabunda×Yellow Magic) not patented, as the seed parent and Gold Badge (Floribunda—U.S. Plant Pat. No. 4,625) as the pollen parent.

Subsequent to origination of the variety I successfully reproduced it, at Sequoia Nursery, located as aforesaid, by budding as well as by cuttings; the reproductions having run true in all respects.

The color photograph illustrates the variety, including the foliage, buds and flowers.

Referring now specifically to the new and distinct variety of miniature rose plant, the following is a detailed description thereof in outline; all major color plate identifications being by reference to the British Colour Council Horticultural Colour Chart, except where common terms of color definition are employed.

Type: Hardy; dwarf; bushy; rounded; upright; seedling; greenhouse; outdoors; cut flowers; garden decoration.

Class: Miniature.

*International identification.*—Variety: Morjoyc.

*Commercial synonym.*—Joycie.

Flowers borne: Often singly but also in loose sprays of 3 to 5 or more on slender wirey stems.

Quantity of bloom: Abundant both outside and in greenhouse.

Bud:

*Peduncle.*—Average length; slender but sturdy; erect; medium green, sometimes lightly tinted bronze (outdoors).

*Hairs.*—Few or none. Before calyx breaks; size — small. Form long; pointed with several small foliaceous apendages and several very small hairs on surface of bud; with foliaceous parts extending beyond the tip of the bud equal to one-half or more of its length.

*Color.*—Medium green, occasionally tinted with bronze (outdoors). As calyx breaks, color — orange to apricot. Opening: opens well in all weather.

Bloom:

*Size when fully open.*—Small, averaging about 35–40 mm (1½").

*Petalage.*—Double — averaging about 30–35 petals arranged regularly plus often several small petaloids.

*Form.*—High centered then becoming more rounded with petals reflexing loosely outward, and later at maturity, rolled loosely outward and downward. Open flowers may show stamens.

Petals: Fairly thick; satiny on inside and on outside surface.

*Shape.*—Outside petals, broad lanceolate with acute tip; intermediate — broad lanceolate with acute tip; inside — lanceolate with acute tip.

Color: Newly opened flower from a plant grown in plastic greenhouse (September 1988), Visalia, Calif.

*Outside petal.*—Outside surface — near Saturn Red 13/1 and blending into yellow on basal ⅓ of petal. Inside surface — bright red orange, near Fire Red 15/1 being lightly veined or underlaid with yellow and blending into yellow on basal ⅓ of petal.

*Intermediate petal.*—Outside surface similar to outside petal. Inside surface — similar to outside petal.

*Inner petal.*—Outside surface — similar to intermediate petal. Inside surface — similar to intermediate petal. General color effect; newly opened flowers — bright orange to red orange. Three days open — color similar but less intense. Behavior — opens well in all weather. Spent petals drop off. Flower longevity (May 1988) — plant in pot 4–5 days or longer. Cut flowers at living room temperature 4–6 days.

Reproductive organs:

*Stamens.*—Several, arranged regularly about pistils.

*Filaments.*—Varying length, medium long, yellow.

*Anthers.*—Yellow.

*Pollen.*—Quite abundant.

*Pistils.*—Average number.

*Styles.*—Fairly even; medium length; bunched; color — reddish.

*Ovaries.*—All enclosed in calyx.

*Hips.*—Fairly plentiful, ball shaped, orange.

*Sepals.*—Permanent; spear shape; recurved against peduncle.

*Seed.*—Several.

Foliage:

*Leaves.*—Compound of five (sometimes three or seven) leaflets; fairly small; leathery; semi-glossy to matt.

*Leaflets.*—Shape: broad, lanceolate; apex acute; base rounded (sometimes acute). Margin serrate. Color: medium to dark green; new growth — normal (medium) green — sometimes reddish (outdoors). Rachis: medium strength; upperside usually quite smooth, grooved; underside sparsely thorny (very small) with few or no tiny prickles. Stipules: short to medium length; narrow to medium width; short length; narrow points which turn out usually at about 45 degrees.

Growth:

*Habit.*—Dwarf; bushy; rounded to upright; much branched.

*Growth.*—Free vigorous; internodes short.

*Canes.*—Medium slender; sturdy.

*Main stems.*—Color: medium green.

*Thorns.*—Few to moderate amount. Prickles — few to none.

*Branches.*—Color: medium green. Thorns: few. Prickles: few to none. Hairs: none.

The miniature rose plant and its flowers as herein described may vary in slight detail due to climatic, soil and cultural conditions under which the variety may be grown; the present description being of the variety as grown at Visalia, Calif.

The following is claimed:

1. A new and distinct variety of miniature rose plant of hardy, dwarf, bushy, rounded to upright, much branched habit, substantially as illustrated and described, characterized by buds and flowers of bright orange to orange red; the bud and flower resembling the variety Sheri Anne (U.S. Plant Pat. No. 3,826) in form; and further characterized by a plant of vigorous and compact growth habit, easy to propagate from cuttings or by budding, with an abundance of small to medium size semi-glossy to matt foliage and an abundance of flowers borne both singly and in loose clusters of 3 to 5 or more.

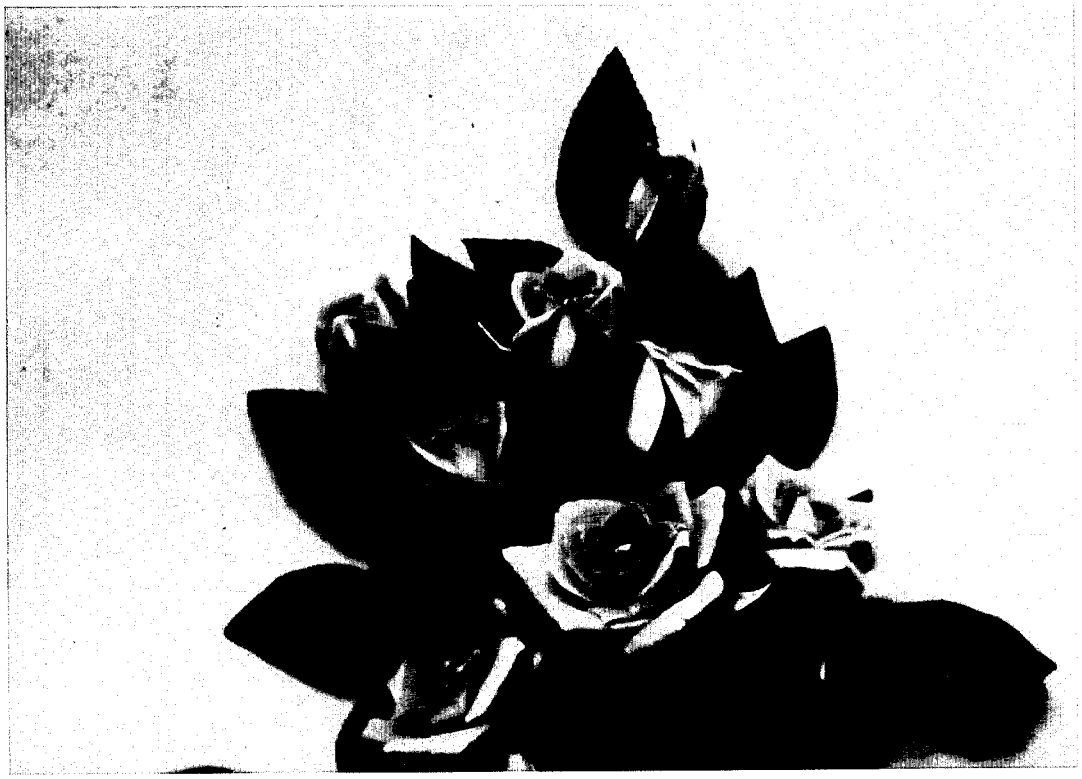

* * * * *